United States Patent [19]

Eisinger

[11] Patent Number: 5,720,981
[45] Date of Patent: Feb. 24, 1998

[54] EPIDERMAL CELL EXTRACTS AND METHOD TO ENHANCE WOUND HEALING AND REGENERATE EPIDERMIS

[75] Inventor: Magdalena Eisinger, Demarest, N.J.

[73] Assignee: Sloan-Kettering Institute for Cancer Research, New York, N.Y.

[21] Appl. No.: 339,573

[22] Filed: Nov. 14, 1994

Related U.S. Application Data

[63] Continuation of Ser. No. 641,318, Jan. 15, 1991, abandoned, which is a continuation of Ser. No. 51,081, May 15, 1987, abandoned, which is a continuation-in-part of Ser. No. 765,711, Aug. 14, 1985, abandoned.

[51] Int. Cl.⁶ ..................................................... A61K 35/36
[52] U.S. Cl. .................. 424/572; 424/570; 424/DIG. 13
[58] Field of Search ........................... 424/520, 572, 424/DIG. 13; 435/70.3, 240.1, 240.2, 240.23, 240.241, 240.243, 240.3, 240.31; 514/21, 925, 928

[56] References Cited

U.S. PATENT DOCUMENTS

| | | | |
|---|---|---|---|
| 3,919,186 | 11/1975 | Ardry et al. | 530/842 |
| 4,254,226 | 3/1981 | Eisinger et al. | 435/240.23 |
| 4,299,819 | 11/1981 | Eisinger et al. | 424/574 |
| 4,423,145 | 12/1983 | Stampfer et al. | 435/240.3 |
| 4,440,860 | 4/1984 | Klagsbrun | 435/240.3 |
| 4,456,687 | 6/1984 | Green | 435/240.3 |
| 4,460,642 | 7/1984 | Errede et al. | 428/422 |
| 4,533,635 | 8/1985 | Guedon born Saglier et al. | 435/240 |

FOREIGN PATENT DOCUMENTS

| | | |
|---|---|---|
| 1132/86 | 2/1987 | Australia . |
| 0013394 | 7/1980 | European Pat. Off. . |

OTHER PUBLICATIONS

Cohen, S., et al. (1975) "Human epidermal growth factor: isolation and chemical and biological properties." *Proc. Natl. Acad. Sci. USA* 72: 1317–1321 (Exhibit 12).

Eisinger, M.G., et al. (1979) "Human epidermal cell cultures: growth and differentiation in the absence of dermal components or medium supplements." *Proc. Natl. Acad. Sci. USA* 76: 5340–5344 (Exhibit 13).

Haigler, H.T., and Cohen, S. (1979) "Epidermal growth factor–interactions with cellular receptors." *Trends in Biol. Sci* 4: 132–134 (Exhibit 14).

Johnson, A.R., et al. (1979) "Growth–promoting actions of extracts from mouse submaxillary glands on human endothelial cells in culture." *Cell Physiol* 101: 431–438 (Exhibit 15).

Liu, S.–C and Karasek, M. (1978) "Isolation and growth of adult human epidermal keratinocytes in cell culture." *J. Invest. Dermatol.* 71: 157–162 (Exhibit 16).

Marcelo, C.L., et al. (1978) "Stratification, specification, and proliferation of primary keratinocyte cultures: evidence of a functioning in vitro epidermal cell system." *J. Cell Biol.* 79: 356–370 (Exhibit 17).

Melbye, S.W., et al. (1973) "Characteristics of a factor stimulating skin epithelial cell growth in vitro." *Exp Cell Res.* 79: 279–286 (Exhbiit 18).

Stampfer, M., et al. (1980) "Growth of normal human mammery cell in culture." *In Vitro* 16: 415–425 (Exhibit 19).

Tzeng, S., et al. (1982) "Partial purification and characterization of an inhibitor from newborn–rat epidermis with activity against the proteinase of *Schistosoma mansoni* cercariae." *Biochem. J.* 207: 479–484 (Exhibit 20).

Hell et al., Br J Exp Pathol 60(2): 171–179 (1979).

Revardel et al., C R Acad Sci III 299 (16): 671–676 (1984).

Tzeng et al Biochem J 207:479–489 1982.

Eisinger et al PNAS 76(10) 5340–5344 1979.

Stampfer, M. et al. (1980), In Vitro 16(5):415–425, Growth of Normal Human Mammary Cells in Culture.

Cohen, S. et al (1975), *PNAS* 72 (4):1317–1321, Human Epidermal Growth Factor: Isolation and Chemical and Biological Properties.

*Primary Examiner*—John W. Rollins
*Assistant Examiner*—Jean C. Witz
*Attorney, Agent, or Firm*—John P. White

[57] ABSTRACT

This invention provides a composition capable of stimulating growth and regeneration of epidermal cells. The composition comprises an aqueous, cell-free extract derived from epidermal cells.

11 Claims, 4 Drawing Sheets

EPIDERMAL CELL EXTRACTS AND METHOD TO ENHANCE WOUND HEALING AND REGENERATE EPIDERMIS

This is a continuation of Ser. No. 07/641,318, filed Jan. 15, 1991, now abandoned, which is a continuation of Ser. No. 07/051,081, filed May 15, 1987, now abandoned, which is a continuation-in-part of Ser. No. 06/765,711, filed Aug. 14, 1985, now abandoned.

This invention was made with government support under grants numbers CA08748 and DAMD-17-85-C-5001 from the National Institutes of Health, United States Department of Health and Human Services and the Unites States Army, respectively. The U.S. Government has certain rights in this invention.

BACKGROUND OF THE INVENTION

Epidermal cells form the uppermost layer of skin and provide an important physiological barrier. Normal undamaged skin is composed of the epidermis and the dermis. Epidermis consists of an inner layer of viable nucleated cells which are covered by laminated cornified cells without nuclei. It contains nerve fibrils, but not blood vessels. The basal layer of the epidermis has irregular ridges (rete ridges) molded against the underlying connective tissue (dermal papillae). The dermis consists of collagen bundles and fibers containing many fixed tissue cells and is richly vascularized by capillaries and venules. Hair follicles, sweat glands and sebaceous glands extend from the dermis to the surface of the skin; such glands and hair follicles are lined by epithelial cells. Underneath the dermis there is an underlying layer of fatty tissue.

Wound treatment

Loss of epidermal coverage by injury or as a consequence of a disease process leaves an open wound which is vulnerable to infection. If this loss is extensive, it also results in excessive loss of fluids and impairment of thermal regulation. When wounded, depending on the depth and the size of the area, regrowth of epidermis will occur from remaining hair follicles, glandular structures or from the side of the wound.

The description of burn wounds is as follows: A first degree burn is superficial; it may remove most of the epidermis and part of the dermis. However, because of the uneven interface between epidermis and dermis, it may leave clusters of intact epidermal cells interdispersed in the damaged area.

A second degree burn is deeper and may renove all epidermal cells, without destroying the epithelial cells that line the hair follicles, sebaceous and sweat glands. In this situation, epithelial cells from the hair follicles and glands can proliferate and migrate over the wound, providing a shallow layer of epidermis. Such a layer is often irregular and fragile and may impede the proper healing of the wound.

A third degree burn is the deepest and destroys all epidermis and dermis, including the follicles, sebaceous glands and sweat glands. It also is termed a "full thickness" wound.

All clinical effort, therefore, is concentrated on achieving the most speedy wound closure. Current methods of treatment are as follows: In burn patients, where a large body area is damaged, surgeons use specially prepared pig skin (xenografts) to provide a mechanical barrier. These xenografts can be kept on the patients for 3-5 days. However, they are rejected if kept longer, leaving again an open wound. Homografts (allografts) can be obtained from human donors (cadavers). They also are in a short supply and are rejected after a brief period of time.

The most effective current treatment involves the use of autografts. Partial thickness sections of the skin are removed from an undamaged area of the patient and transplanted on the wounded area. They become permanently attached and proliferate. If the wounded area is extensive and the skin available is limited, then burn surgeons use small patches of skin (approximately 5×3 cm) spaced at distance of 3-5 cm apart. These areas are eventually covered by the outgrowth of epidermis from the transplanted pieces of split thickness skin.

The removal of the skin for grafting is usually performed with an instrument called a dermatome. The thickness of the removed skin can be controlled. Because of the papillary nature of the epidermis, even with the thinnest cut, all epidermis and some of the dermis is removed by this procedure. This harvesting operation is a painful, invasive process and causes scarring.

Autografts may be repeatedly harvested from the donor site, after it heals. Additionally, in order to cover a larger area, autografts can be meshed by a device which slits the skin in a regular pattern and enlarges the piece of skin approximately 10 fold. The space caused by the slits is eventually filled by cells growing from the sides.

All of the above-mentioned modes of treatment, however, are time consuming, costly and lead to various problems such as hypertrophic scarring and contracture. Therefore, there exists a need to provide prompt functional coverage and prevent scar formation in deep and extensive wounds.

The Role of Growth Factors in Epidermal Regeneration

In contrast to the well known and accepted regulatory effects of the dermis on epidermal cells, the effects of epidermis on dermis have not been studied extensively. Most research concerning growth regulation by epidermal cells concentrated on epidermal inhibitors termed chalones, as it was believed that they might be the sole regulators of epidermal regeneration. Advances in cellular and molecular biology, however, have made it possible to define the role of cellular products (growth factors) in regulation of growth and differentiation of cells. Suggestions have been made that certain known growth factors such as epidermal growth factor (EGF), platelet derived growth factor (PDGF), transforming growth factor (TGF-α or TGF-β), urogastrone and factors produced by fibroblasts and epidermal cells may be useful in promoting wound healing and epidermal regeneration. None of these factors, however, are derived from epidermal cells. Also, current information about the effects of growth factor(s) on isolated populations of cells has been obtained mainly by studies in vitro.

In response to the shortcomings of the prior art, this invention provides a composition capable of stimulating growth and regeneration of epidermal cells and methods for enhancement of wound coverage and healing, suppression of fibroblast proliferation and prevention of scar formation.

The invention is advantageous in that it may be used for wounds or burns to enhance healing, reduce the covering time and reduce the possibility of any resulting infection or trauma. It also may reduce the healing time of a surgical incision. Additionally, the invention may be used to enhance the growth of allogeneic, autologous or xenogeneic transplanted skin material. Furthermore, the invention may have cosmetic value to remove or ameliorate age spots on skin. It also is possible that the composition of this invention may provide skin regeneration in situ, or its effects may stabilize hair growth. Finally, the composition of this invention may be useful internally to heal chronic wounds, such as ulcers, or blistering skin diseases such as epidermolysis bullosa.

SUMMARY OF THE INVENTION

This invention provides a composition capable of stimulating growth and regeneration of epidermal cells. The composition comprises an aqueous, cell-free extract derived from epidermal cells.

This invention also provides a method for stimulating the growth or regeneration of epidermal cells in a subject whose epidermal cells are not growing or regenerating adequately. The method comprises contacting the subject's epidermal cells with an amount of the composition of this invention effective to stimulate adequate growth or regeneration of epidermal cells.

Moreover, this invention provides a method for enhancing wound coverage and healing in a wounded subject. The method comprises contacting the subject's wound with an amount of the composition of this invention effective to stimulate the growth of epithelial cells and thereby enhance wound coverage and healing.

This invention further provides a method for enhancing the wound coverage of transplantated skin material situated on a wounded region of a subject. The method comprises contacting the transplanted skin material with an amount of the composition of this invention effective to enhance wound coverage.

Additionally, this invention provides a method for stimulating the suppression of fibroblast proliferation in a wounded region of a subject. The method comprises contacting the subject's wounded region with an amount of the composition of this invention effective to stimulate the suppression of fibroblast proliferation in the wounded region.

This invention also provides a method for preventing scar formation at the site of a wound in a wounded subject. The method comprises contacting the subject's wound with an amount of the composition of this invention effective to prevent scar formation.

Moreover, this invention provides a composition of matter capable of stimulating epidermal cell growth and regeneration, derived from an aqueous, cell-free extract of epidermal cells.

Finally, this invention discloses a wound dressing comprising an effective wound healing amount of the composition of this invention and a permeable solid matrix carrying the composition.

BRIEF DESCRIPTION OF THE FIGURES

These figures show a histological section of a biopsy specimen from a wound treated with the epidermal cell extract (left panel) and a control wound (right panel). FIG. 1A and FIG. 1D show 5 days, FIG. 1B and FIG. 1E show 12 days and FIG. 1C and FIG. 1F show 23 days after wounding. Note that on days 5 and 12, the control wound was not covered by epidermis, while the treated ones on day 12 had a functional coverage. The hyperplastic epidermis returned to normal 23 days after wounding.

Figure 1A:
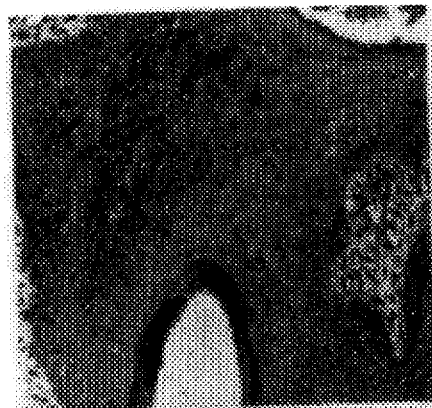
FIGS. 1A–1F

This figure shows tissue culture studies of collagen contraction by fibroblasts. "A" shows contraction by fibroblasts. "B" show spontaneous collagen contraction after 3 days of exposure to tissue culture medium.

FIG. 3

This figure shows tissue culture studies of collagen contraction by fibroblasts. "A" shows that epidermal cell extracts prevented contraction caused by fibroblasts. "B" shows that epidermal cell extracts subjected to heat treatment (60° C.) have lost some activity. "C" shows that cell activity was destroyed by acid treatment (pH 3.0).

FIG. 4

This figure shows the effects of epidermal cell extracts and other known growth factors on collagen contraction by fibroblasts. C is the control, seeded by fibroblasts. B is the control not containing cells. A is NGF (nerve growth factor), B is EGF (epidermal growth factor) C is TGF-$\beta$ (transforming growth factor-$\beta$) and E is the epidermal cell extract. Note that only epidermal cell extract suppressed collagen contraction by fibroblasts.

DETAILED DESCRIPTION OF THE INVENTION

This invention provides a composition capable of stimulating growth and regeneration of epidermal cells. The composition comprises an aqueous, cell-free extract derived from epidermal cells. Preferably, the epidermal cells of the composition are of human or porcine origin. Presently, cultured epidermal cells are preferred. Alternatively, the epidermal cells used in the practice of this invention may be taken directly from a subject and used without further growth or treatment.

This invention also provides a method for stimulating the growth or regeneration of epidermal cells in a subject whose epidermal cells are not growing or regenerating adequately. The method comprises contacting the subject's epidermal cells with an amount of the composition of this invention effective to stimulate adequate growth or regeneration of epidermal Cells. In the preferred embodiment, the subject is a mammal, particularly a human, swine, horse or dog. Various regimens may be employed for contacting the subject's wound with the composition of this invention so as to enhance wound coverage and healing in the wounded subject. In the preferred embodiment, the contacting comprises contacting the wound with a permeable solid matrix carrying the composition of this invention. The solid matrix may be any one of the well known standard, nonadhesive dressings. Alternatively, the composition may be lyophilized and used for skin treatment either in the form of a spray or a powder, or it may be mixed into a cream. Additionally,. it may be possible to spray the composition onto the wound, in vivo, or onto the cells, in vitro.

Moreover, this invention provides a method for enhancing wound coverage and healing in a wounded subject. The method comprises contacting the subject's wound with an amount of the composition of this invention effective to stimulate the growth of epithelial cells and thereby enhance wound coverage and healing.

This invention further provides a method for enhancing the wound coverage of transplantated skin material situated on a wounded region of a subject. The method comprises contacting the transplantated skin material with an amount of the composition of this invention effective to enhance wound coverage.

The presently preferred transplanted skin material is tissue culture grown epidermal cells. In the preferred embodiment, the transplanted skin material is either autologous or allogeneic relative to the subject.

Additionally, this invention provides a method for stimulating the suppression of fibroblast proliferation in a wounded region of a subject. The method comprises contacting the subject's wounded region with an amount of the composition of this invention effective to stimulate the suppression of fibroblast proliferation in the wounded region.

This invention also provides a method for preventing scar formation at the site of a wound in a wounded subject. The method comprises contacting the subject's wound with an amount of the composition of this invention effective to prevent scar formation.

Moreover, this invention provides a composition of matter capable of stimulating epidermal cell growth and regeneration. The composition of matter is derived from an aqueous, cell-free extract of epidermal cells.

The invention further discloses a pharmaceutical composition comprising an amount of the composition of matter of this invention effective to stimulate growth and regeneration of epidermal cells and a pharmaceutically acceptable carrier.

Finally, this invention discloses a wound dressing comprising an effective wound healing amount of the composition of this invention and a permeable solid matrix carrying the composition.

Experimental Results

The invention is exemplified by the series of experiments which follow. These experiments reveal that epidermis is producing factor(s) that have a stimulatory effect on growth of epidermal cells, as well as an inhibitory effect on the proliferation or migration of fibroblasts in healing wounds. These findings imply the possible role of locally produced factors (s) in both positive and negative feedback mechanisms and maintenance of homeostasis in the epidermis and dermis.

The role of different growth factors in wound healing currently is widely studied. Autocrine regulators previously identified in epidermal cells have been found to be potent inhibitors (e.g., chalones). It, therefore, was widely believed that epidermal cell growth was solely regulated by negative feedback. Factors that stimulate epidermal cell growth, such as epidermal growth factor, its human analog, urogastrone, and closely related TGFα, have been isolated from tissues other than epidermis. The findings presented here indicate that epidermal cells are capable of producing factor(s) that locally stimulate proliferation of epidermal cells. EGF has been long suggested to play a role in wound healing, as, it is present in saliva and animals that lick their wounds. Application of EGF of TGFα to experimental wounds has been shown to accelerate reepithelization and promote connective tissue formation in healing wounds. EGF and TGF have been shown to promote general growth of epidermal cells. in vitro, while the experiments disclosed herein suggest that the epidermal cell extract of this invention may effect only a selected subpopulation of epidermal cells, namely the stem cells. This is revealed by the appearance of colonies of epidermal cells resembling those recently described in the prior art. The limited numbers of colonies seen in the experiments disclosed herein can be attributed to low numbers of stem cells in epidermis and possibly loss in the separation procedure. Alternatively, the profound in vivo effect of epidermal cell extract (ECE) may be: i) potentiated by extracellular matrix materials or by other growth factors present in the wound, or ii) mediated by another cell type.

It is well accepted today that wound healing occurs by two intentions: i) wound closure (contracture), and ii) reepithelization; a concept originally presented in the prior art. The contracture is most prominent in animals with loose integument, such as mice or rabbits, and is less in those having a close association of integument with underlying tissue (e.g., pig). The cells responsible for contracture are the fibroblasts, or so called myofibroblasts. The negative regulatory effect of ECE(s) on fibroblasts was shown both in vivo and in vitro. The in vivo experiments indicated that, in comparison to the control or other growth factors, wounds that were treated with epidermal cell extract showed a hypocellular newly formed granulation tissue. The density of fibroblasts in ECE-treated wounds closely resembled those of a non-wounded area.

Fibroblasts grown in tissue culture resemble myofibroblasts. A system to study contracture of collagen gels by fibroblasts in vitro has been studied in the prior art and it has been shown that the rate of collagen shrinkage is proportional to the density of fibroblasts present in the collagen gel. In the experiments disclosed herein, it was shown that prefabricated collagen sponges were seeded by fibroblasts and induced to shrinkage. This shrinkage was completely inhibited by ECE (s) , but not by other known growth factors. ECE(s), therefore, either by regulating the numbers of fibroblasts or by influencing their state (replicating versus stationary), regulated contraction of collagen matrices.

Another important question examined was whether rapidly proliferating versus stationary fibroblasts produced different types of collagen which contributed to scar formation. It is well known that newly formed granulation tissue contains mainly type III collagen characterized by thin filaments. Similarly, there is more type III and type V collagen in hypertrophic scars. In the wounds treated with ECE, however, the bundles of collagen matrix strands were seen as early as 5 days after wounding, suggesting that type I collagen might have been synthesized by resident fibroblasts, resulting in less contraction, and no scaring. Success in the experimental treatment of horses with ECE immediately after surgical removal of excessive granulation tissue strongly supports the findings that ECE(s) suppresses formation of granulation tissue. The fact that these horse wounds, as well as the perianal ulcers of dogs, reepithelized, supports the findings that ECE(s) promotes wound reepithelization. The inventor contemplates that the factor (s) responsible for promoting reepithelization and suppressing fibroblasts are the same or similar molecules.

The experiments also have shown that both properties, suppression of fibroblast proliferation and reepithelization, were abolished by acid treatment, but sustained heat (60° C.) and alkaline treatment. Another factor (TGFβ) has been shown to have either growth promoting or growth suppressing effects on different cell types. It, therefore, may be that the epidermis produces a molecule responsible for both positive and negative regulatory effect in the skin.

Method

The growth of epidermal cells in vitro, the preparation of epidermal cell extract and the application of epidermal cell extracts was the same in all the experiments described herein.

Epidermal growth factor (EGF) and nerve growth factor (NGF) were purchased from Collaborative Research Inc. Bedford, Mass. Transforming growth factor (TGF-α) was purchased from Peninsula Laboratories Inc., Belmont Calif. Transforming growth factor (TGF β) and Fibroblast growth factor-β (FGF-β) were gifts.

Growth of Epidermal Cells

The epidermis of human skin was separated from the dermis using the Medawar trypsin technique. Nature, 148, 783-4 (1941). The separated epidermis was dissociated into individual epidermal cells mechanically and the cells were then seeded into a suitable tissue culture medium at the required pH. It was preferable to remove any remaining clumps or pieces of tissue, for example, by filtration, prior to seeding. This removes non-viable cells that otherwise would interfere with growth of the epidermal cells.

The suitable tissue culture medium had a pH in the range of about 5.9–6.6 and supported and promoted the growth of the epidermal cells. The growing was preferably carried out in a plastic tissue culture vessel, but other cell growth techniques also could have been used.

A preferred culture medium contained about 5–15% by volume, preferably about 10%, fetal calf serum which was commercially available from a number of sources. Hydrocortisone could be added to the medium to make the colony morphology more orderly and distinctive. Rheinwald and Green, Cell, 6, 331–44 (1975). It also was desirable to reduce the amount of fetal calf serum to about 5% once the cells become attached to the vessel.

Seeding of the epidermal cells in the culture medium was preferably in the range of about $5–8\times10^5$ cells/ml, which had been found to promote optimal growth of the epidermis.

Growth in the medium was preferably carried out at a temperature of about 35°–36° C., under relative humidity of about 80% in the presence of 5% carbon dioxide and 95% atmospheric air.

Preparation of the epidermal cell extract:

Confluent cultures of epidermal cells (grown in vitro for 3–6 weeks) were washed twice with phosphate buffered saline and removed by scraping using a rubber policeman. The cells were pelleted at 180 g for 10 minutes, and resuspended in an equal volume of phosphate buffered saline (PBS), sonicated twice for 15 seconds, and diluted 1:10 with phosphate buffered saline. The suspension was clarified by two consecutive ultracentrifugation steps at 16,000 g for 20 minutes and 150,000 g for 45 minutes. The resulting clarified cell extract was aliquoted and frozen at −70° C. To collect the secreted factor, epidermal cells grown to confluency were washed with PBS and fed with medium containing no fetal calf serum. The supernatants were collected 24 and 48 hours later.

Application of the epidermal cell extracts (ECE)

Clarified supernatants were applied to an open wound using an absorbing material (e.g., Release, a non-adhesive dressing manufactured by Johnson & Johnson).

First Series of Experiments

Method

Wound Healing Assay

Domestic outbred swine were anaesthesized by ketamine hydrochloride, followed by a mixture of halothane, nitrous oxide and oxygen. They were shaved and the area of skin was washed twice with Betadine and then with 70% alcohol. Wounds 0.040 inches (1 mm) deep were created with a Brown dermatome on the lateral side. This corresponds to a deep second degree burn and removes all the epidermis and most of the dermis. Deep hair follicles and associated glandular structures were left in the wound bed. Some of the wounds were approximately 6 inches by 3 inches. The majority of the wounds were approximately 2.5 inches by 2.5 inches. There were 2–3 dorsal lateral wounds per animal.

Nonadhesive dressing (Release, Johnson & Johnson) was cut to fit the size of the wound, soaked in the tested materials and applied to the wound bed. The dressing was covered by multiple layers of gauze and held in place by silk ligatures. The pig was bandaged with Elastoplast. After 5 days the dressing was removed and wounds were covered once more with Release, prewetted with Ringers solution, and gauzed and bandaged with Elastoplast. Following surgery, the pigs received analgesics to alleviate pain. The wounds were observed in 2–4 day intervals at which time 3 mm punch biopsies were taken from the center of the wound. Wounds were left uncovered usually 12–14 days post surgery.

Histology

Three millimeter punch biopsies were fixed in Bouin's solution overnight and embedded in paraffin. Sections were cut and stained with heamatoxylin and eosin. Evaluation of the sections was done using a light microscope. The central area in the new granulation tissue was selected and the distance between the nuclei of adjacent fibroblasts was measured in microns using a calibrated occular. Evaluation of epidermal cells was done by counting the number of epidermal cell layers arising from hair follicles in the new granulation tissue.

Stimulation of growth of epidermal cells in vitro

An epidermal single cell suspension was prepared. $7.5\times 10^4$ cells were seeded in a 12 well plate (Costar, Cambridge, Mass.) in minimal essential medium containing antibiotics and supplemented with 10% Fetal bovine serum (c MEM). Tested samples at different dilutions were added at the time of plating or 24 hours later. The medium was changed in 3 day intervals. After 8 days of incubation at 36° C., the cells were fixed with buffered formaldehyde and stained. Numbers of colonies and numbers of cells per colony were counted under the microscope.

Fibroblasts in collagen sponges

Pig or human fibroblasts were derived from normal skin and grown in tissue culture in cMEM. Fibroblasts passaged in culture 4–8 times were used for the experiments. Collagen sponges 2 mm thick made of type I bovine collagen were purchased from Biomaterials Center, Piscataway, N.J. They were cut into circles of 3.2 cm in diameter and placed into plastic dishes (Costar, Cambridge, Mass.). $0.8\times 10^6$ cells were seeded per 8 cm$^2$ area in c MEM. Six hours later the medium was changed and substances to be tested were added in c MEM. Shrinkage of collagen sponges was measured daily. The experiments were terminated 4 to 8 days after addition of factors.

Results and Discussion

Clinical Response To Epidermal Cell Extract

Gross Appearance: The response to the standard wound (depth $40\times 10^{-3}$ in.) in untreated (control) areas was a short period of hemorrhage followed by drying of the exudate and scab formation over 24 hours. No appreciable epidermal growth was seen for the next 6–7 days. On the eighth day, epidermis could be observed moving in from the edges of the wound and from epidermal remnants (hair follicles and skin glands). The surface of the wound showed continuing signs of inflammation and some degree of exudation. Epithelialization was normally complete by 10 to 12 days after injury.

In wounds that had been treated with the epidermal cell extract, the clinical picture was strikingly different. Epithelial growth was clearly visible by day 3 and the inflammatory response less pronounced at this time than in the untreated wounds. By day 5, epithelialization was well established and signs of hair growth in the wound area were noticeable. By day 10, the gross differences between the control and treated wounds were becoming less pronounced and by day 15 they had disappeared, except that the hairs in the treated areas were longer and more abundant.

Histology

Figure 1D:

Biopsy specimens taken from control and the ECE-treated areas confirmed that epidermal regeneration began 4 days earlier in the latter regions and proceeded rapidly from all epidermal remnants. FIG. 1A shows a section taken at day 5 from an ECE-treated wound in the region of a hair follicle from which extends numerous branches of rapidly proliferating epidermal cells with many mitotic figures. The epidermal cells have penetrated the new granulation tissue which contained many inflammatory cells and began to spread out in a thin layer (1–4 cells thick) over its surface, under the crust of exudate. Serial sections showed that the new epidermal cells were of multiple origin, arising from the several epithelial structures remaining in the undamaged, deeper parts of the dermis. At this stage of healing, the new granulation tissue in the treated areas was highly vascular. The appearance of this section contrasted with that of an untreated, control wound of the same age on the same pig (FIG. 1D) where there was virtually no evidence of epithelial activity but extensive connective growth, a high degree of vascularity and many inflammatory cells on the unhealed surface.

In ECE-treated wounds, the epidermal cells spread rapidly over the surface of the exposed connective tissue and produced complete coverage before day 8, by which time there was a continuous multicellular, hyperplastic layer of new epidermal cells. Under this epidermal covering, the granulation tissue appeared to be maturing and the small blood vessels which had previously been so prominent were at this point less obvious and disappearing or collapsing. In general, connective tissue proliferation in the ECE-treated wounds appeared to be inhibited as compared to that in the controls; cellularity was decreased while new collagen matrix strands became apparent early.

By day 8 in the control sections, the epidermal cells were multilayered, but uneven in thickness. The new granulation tissue was observed to be much thicker than in the ECE treated section, to have a highly active appearance and to contain large, dilated blood vessels.

Figure 1B:
Figure 1E:

On day 12 (FIG. 1B) in ECE-treated wounds, the epidermis showed few mitoses and the thickness was less than at 8 days. The rete pegs were shorter and the connections to the deep epidermal structures were being lost. The depth of the new granulation tissue was substantially less and the vascularity greatly reduced as compared to that in the control wounds (compare FIG. 1B and FIG. 1E) where the rete pegs also remained obvious. There was considerable vascularity, with relatively large vessels prominent in the new dermis, and the epidermis was still hyperplastic.

Figure 1C:
Figure 1F:
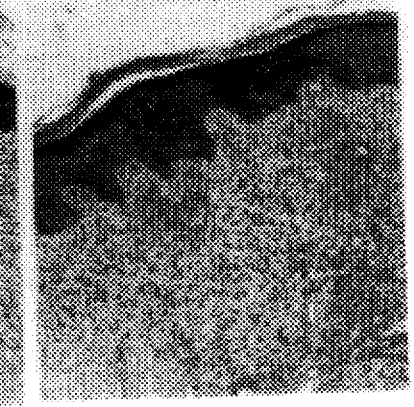

By day 23 there was little difference between the biopsies taken from the control and the experimental groups, except that as shown in FIGS. 1C v. 1F, the new connective tissue layer was considerably thicker in the control than in the treated region and some mitotic activity was still present in the basal layer of the epidermis of the control sections.

Table 1 summarizes the evaluation of histological specimens obtained 8 days after treatment of experimental wounds with epidermal cell extracts at 1:200 dilution and compares it to the controls treated with phosphate buffered saline or 200 ng/ml EGF, urogastrone or TGFα and normal unwounded skin. The density of fibroblasts per cm$^2$, calculated on the basis of measurements obtained from distances between nuclei of resident fibroblasts in the dermis, was found to be the lowest (0.11×10$^6$) in experimental wounds treated with epidermal cell extracts, this resembling normal unwounded skin. The high cellularity seen in the PBS control (1.4×10$^6$) also was observed in wounds treated with EGF and urogastrone. The highest numbers of fibroblasts were seen in wounds treated with TGFα. On the contrary, epidermal cells were most stimulated by epidermal cell extracts and EGF.

TABLE 1

THE EARLY EFFECTS OF GROWTH FACTORS ON WOUND HEALING

| FACTOR | FIBROBLASTS | | | EPIDERMAL CELLS |
|---|---|---|---|---|
| | DIST. BETWEEN NUCLEI (μm ± S.E.M.) | DENSITY/cm$^2$ | % | TOP/ SPROUTS |
| ECE | 30 ± 10 | 0.11 × 10$^6$ | 7.8 | 7/77 |
| EGF | 13 ± 4.3 | 0.6 × 10$^6$ | 42.8 | 1/30 |
| UROG. | 9 ± 3 | 1.2 × 10$^6$ | 85.7 | 2/25 |
| TGF-α | 8 ± 2.6 | 1.6 × 10$^6$ | 114 | 0–4/0 |
| PBS | 8.5 ± 2.8 | 1.4 × 10$^6$ | 100 | 1–2/0 |
| NORM. SKIN | 40 ± 13.3 | 0.06 × 10$^6$ | 4.3 | 0–4/0 |

Table 1 shows a comparison of the effects of ECE (epidermal cell extract) and other known growth factors such as EGF (epidermal growth factor), urogastrone, TGF-α (transforming growth factor α) and PBS (phosphate buffered saline) on reepithelization and the density of fibroblasts. The values also are compared to normal (unwounded) skin. Note that the epidermal cell extract had the most pronounced effects on epidermal cell growth and suppression of fibroblast proliferation (evaluation from histological section) 7 days after woundings.

Second Series of Experiments

Method

The methods employed in this series of experiments were the same as those employed in the first series of experiments, except that these methods were performed in culture.

Results and Discussion

Experiments in tissue culture confirmed the observation in vivo. It was found that epidermal cells grown in the presence of epidermal cell extract extracted from human or porcine epidermal cells had a better plating efficiency and formed colonies of rapidly growing cells even when plated at low seeding densities (1×10$^4$ cells/60 mm Petri dish). Controls at this cell density, in the absence of epidermal cell extract, did not grow. Additionally, when plated at optimal seeding densities (5×10$^5$/60 mm Petri dish), replication began much earlier than in the absence of the epidermal cell extract or in the presence of an extract from other cells such as WI-38.

Figure 2:
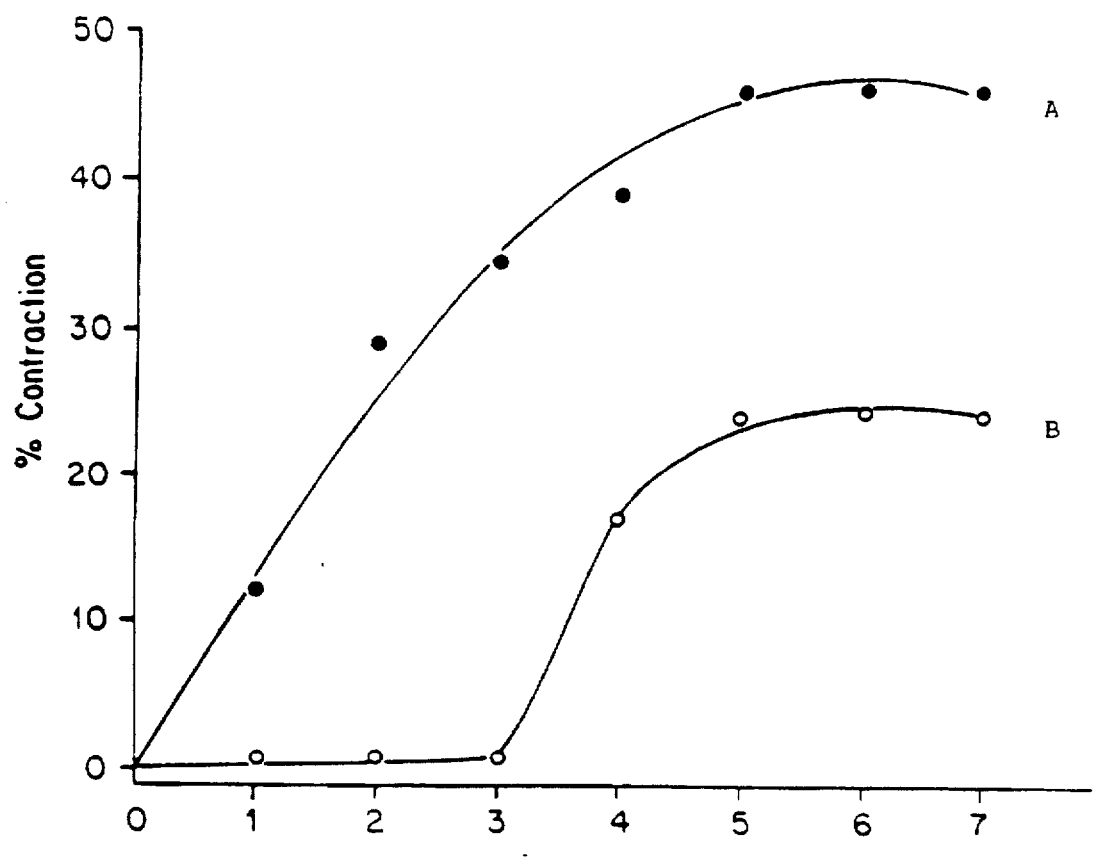
FIG. 2
Figure 3:
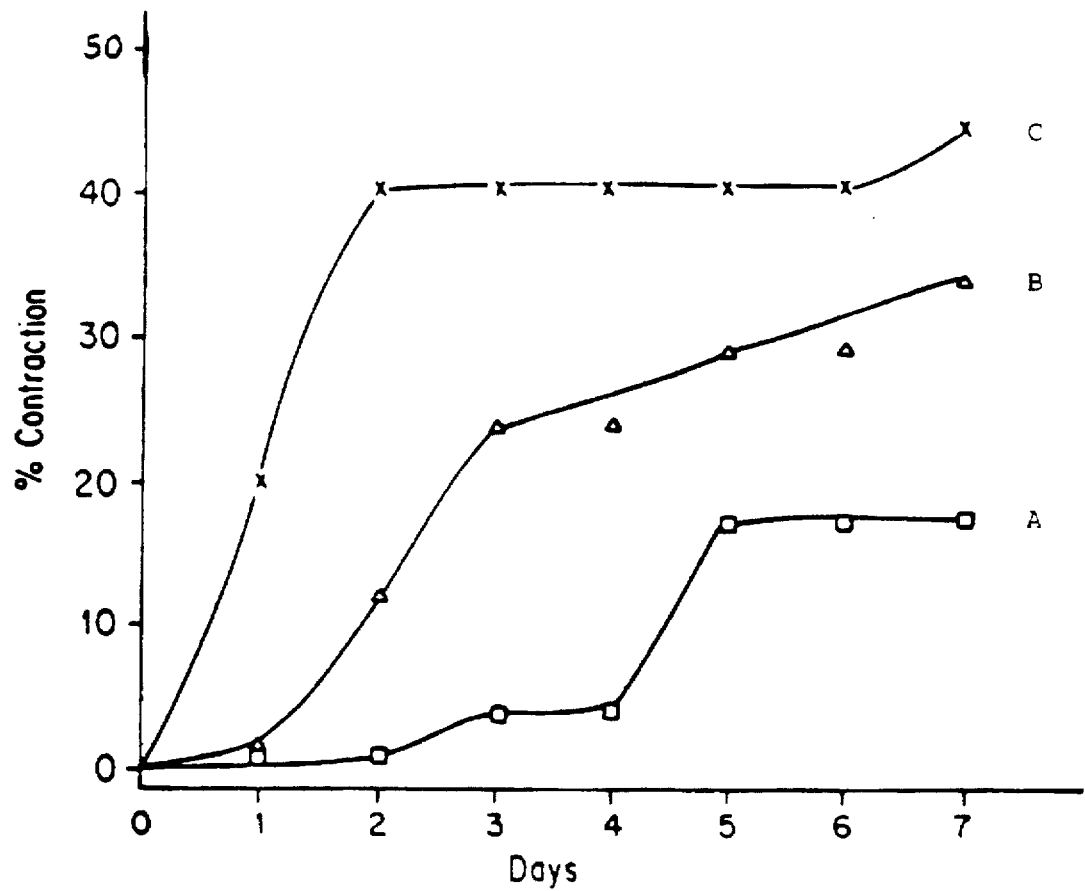

In vitro results of collagen contraction by fibroblasts showed that accelarated shrinkage caused by fibroblasts was observed in the first 4 days (FIG. 2), at the time when the fibroblasts were actively proliferating. The control collagens, not containing cells, did not shrink for the first 3 days, but contracted 20% between days 3 and 4. As shown in FIG. 3, contraction by ECE was inhibited throughout the observation period. The 17% contraction observed at days 5,6,7 was non-specific, as it also was seen in the control gels not containing cells. Heat treatment (60° C. for 2 hours) lowered the activity of the cell extract, while acid treatment caused complete loss of activity. A control cell extract from WI-38 cells did not show any contraction inhibiting activity and the shrinkage was identical to that seen with the control gels containing cells.

Figure 4:
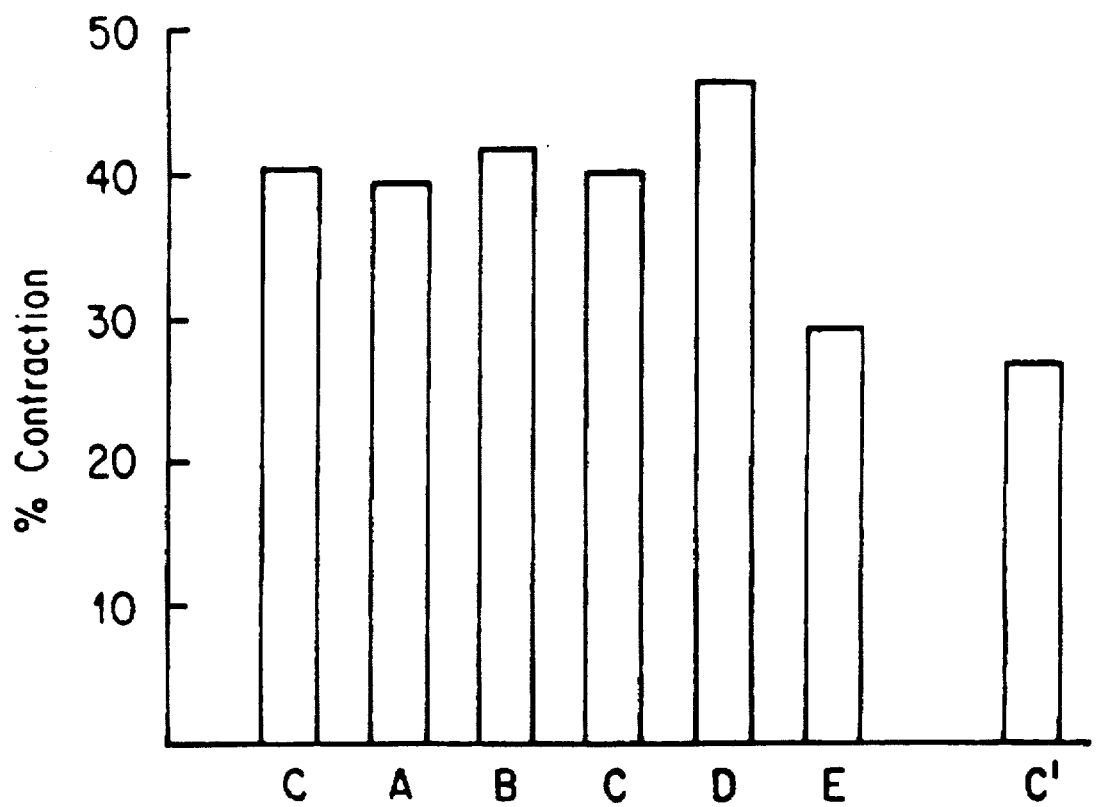

FIG. 4 compares the effects (after 4 days) of ECE on collagens seeded with fibroblasts, with the effects of other factors, such as nerve growth factor (NGF), epidermal growth factor (EGF), fibroblast growth factor-b (FGF), TGFβ and control collagens with and without fibroblasts. The contraction caused by fibroblasts was not inhibited by any of these growth factors, but the contracture was inhibited by the presence of ECE in the culture medium. These results, similar to those seen in vivo, indicate that known growth factors, such as EGF, TGFα, urogastrone, NGF, and FGF do not suppress growth of fibroblasts in vivo, and do not interfere with collagen shrinkage in vitro.

To show the in vitro effect of the epidermal cell extract on the growth of epidermal cells has proven to be difficult. $^3$H-thymidine uptake and cell counts of the first passage of keratinocytes did not show any significant differences when ECE was present or absent in the culture medium. Similarly, colony counts using a culture system known in the art did not show any stimulating effect of ECE.

When epidermal cells were plated at cloning density in the absence of feeder layer, the colonies obtained were in the range of 50 cells or more in the presence of ECE. However, no colonies of this size were seen in medium not containing ECE. The numbers of large colonies were small (0.05% of the cells attached). These colonies were composed of a homogeneous population of small cells with large nuclei. This was contrasted by many large differentiated cells seen in small colonies in the control. It, therefore, appears that ECE can stimulate growth of a selected subpopulation of epidermal cells.

Third Series of Experiments

The methods employed herein were the same as those previously described in the first two series of experiments. The wounded area, however, corresponded to a third degree burn and as such, there were no epithelial remnants. Epidermal cells, therefore, had to be introduced into the wound. For this purpose, small pieces of autologous skin, or skin grown in tissue culture were used. It was found that simultaneous application of the epidermal cell extract enhanced the outgrowth of epidermal cells from transplanted epidermal cells and enhanced full coverage of the wounded area.

Fourth Series of Experiments

Clinical treatment of horses and dogs

Horses suffering from long-term unhealing wounds on the lower parts of the limbs were used for clinical studies. Four horses with severe lacerations of the metacarpal region of the forelimbs that had resulted in non-healing exuberant granulation tissue protruding from the wound site (a common feature of wounds on the lower parts of the limbs of horses) were treated over 10 days by three sets of dressings soaked in a solution of ECE starting immediately after surgical removal of the excessive granulation tissue. Previous excisions had been performed, but the granulation tissue regrew before epithelialization was able to cover the wound. A fifth horse with a non-healing, ulcerated traumatic injury in the same region was treated with a similar ECE regime after the wound surface had been debrided of necrotic material. They were treated over 10 days by 3 sets of dressings soaked in ECE.

One of the more intractable sequelae of impaction of the perianal sacs of dogs is chronic, destructive ulceration of the perianal and pudendal regions. Dogs suffering from destructive ulceration of the perianal and pudenal regions were treated with the epidermal cell extract. Three long established (more than six months) cases were treated by application of ECE-soaked dressings over period of 10 days.

Results And Discussion

Accidental Clinical Injuries in Horses

In the four horses with severe lacerations of the metacarpal region of the forelimb, new epidermal growth appeared from the edges of the wound and from isolated epidermal remnants, in one case by day 4 and in the others by day 6 of ECE treatment. In the fifth horse, there appeared to be no response to the ECE.

Complete healing of the lesion took between 17 and 35 days. This reflected the variation in the size of the area to be covered by epithelium. A common feature of all five cases was that regardless of whether the epithelium was stimulated to grow, the excessive proliferation of granulation tissue that had been a feature of four of the lesions was clearly suppressed by the ECE treatment.

Spontaneous Perianal Ulceration in Dogs

Two of the dogs responded favourably and the ulcerated areas healed over the following 24 and 35 days respectively. In the third case, there was an initial appearance of epidermal stimulation, but this was transitory and destructive ulceration continued after an intermission of about 7 days.

What is claimed is:

1. A method for stimulating growth or regeneration of epidermal cells in a subject which comprises contacting the subject's epidermal cells with an amount of a composition that will stimulate growth and regeneration of epidermal cells and inhibit migration of fibroblasts and contraction of collagen consisting essentially of a clarified aqueous, cell-free extract derived from epidermal cells effective to stimulate growth or regeneration of epidermal cells.

2. The method of claim 1, wherein the subject's epidermal cells are contacted with a permeable solid matrix carrying the cell-free extract derived from epidermal cells.

3. The method of claim 1, wherein the subject is a mammal.

4. The method of claim 3, wherein the mammal is a human, swine, horse or dog.

5. A method for enhancing wound coverage and healing in a wounded subject which comprises contacting the subject's wound with an amount of a composition that will stimulate growth and regeneration of epidermal cells and inhibit migration of fibroblasts and contraction of collagen consisting essentially of a clarified aqueous, cell-free extract derived from epidermal cells effective to stimulate the growth of epithelial cells and thereby enhance wound coverage and healing.

6. A method for enhancing the wound coverage of transplantated skin material situated on a wounded region of a subject which comprises contacting the transplanted skin material with an amount of a composition that will stimulate growth and regeneration of epidermal cells and inhibit migration of fibroblasts and contraction of collagen consisting essentially of a clarified aqueous, cell-free extract derived from epidermal cells effective to enhance wound coverage.

7. A method of claim 6, wherein the transplantated skin material is autologous relative to the subject.

8. A method of claim 6, wherein the transplantated skin material is allogeneic relative to the subject.

9. A method of claim 6, wherein the transplantated skin material is tissue culture grown epidermal cells.

10. A method for inhibiting fibroblast proliferation in a wounded region of a subject which comprises contacting the subject's wounded region with an amount of a composition that will stimulate growth and regeneration of epidermal cells and inhibit migration of fibroblasts and contraction of collagen consisting essentially of a clarified aqueous, cell-free extract derived from epidermal cells effective to inhibit fibroblast proliferation in the wounded region.

11. A method for preventing scar formation at the site of a wound in a wounded subject which comprises contacting the subject's wound with an amount of a composition that will stimulate growth and regeneration of epidermal cells and inhibit migration of fibroblasts and contraction of collagen consisting essentially of a clarified aqueous, cell-free extract derived from epidermal cells effective to prevent scar formation.

* * * * *